United States Patent  
Adair et al.

(10) Patent No.: US 7,651,666 B2
(45) Date of Patent: Jan. 26, 2010

(54) AIR TREATMENT DEVICE WITH RESERVOIR REFILL

(75) Inventors: Joel E. Adair, Racine, WI (US); Brian T. Davis, Burlington, WI (US); Gopal P. Ananth, Racine, WI (US); David P. Mather, Milwaukee, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 530 days.

(21) Appl. No.: 11/379,495

(22) Filed: Apr. 20, 2006

(65) Prior Publication Data

US 2007/0248502 A1  Oct. 25, 2007

(51) Int. Cl.
| | |
|---|---|
| *A61L 9/00* | (2006.01) |
| *A62B 7/08* | (2006.01) |
| *A01G 13/06* | (2006.01) |
| *A01M 13/00* | (2006.01) |
| *A21B 1/00* | (2006.01) |
| *F27D 11/00* | (2006.01) |
| *H05B 3/06* | (2006.01) |
| *B65H 1/00* | (2006.01) |
| *B65G 59/00* | (2006.01) |
| *A24F 25/00* | (2006.01) |
| *B01D 47/00* | (2006.01) |

(52) U.S. Cl. ............... 422/123; 422/1; 422/5; 422/28; 422/124; 422/125; 422/306; 422/307; 392/386; 392/390; 392/391; 392/392; 392/393; 43/1; 43/124; 43/125; 219/392; 219/541; 219/524; 219/435; 221/197; 221/287; 239/34; 239/60; 239/57; 239/136; 261/26; 261/101; 261/104; 261/89

(58) Field of Classification Search ............ 422/1, 422/5, 28, 123–125, 306–307; 392/386, 392/390–393; 43/1, 124–125; 219/392, 219/541, 524, 435; 221/197, 287; 239/34, 239/60, 57, 136; 261/26, 101, 104, 89
See application file for complete search history.

(56) References Cited

U.S. PATENT DOCUMENTS

| | | | |
|---|---|---|---|
| 2,435,756 A | | 2/1948 | Schlesinger |
| 3,014,353 A | | 12/1961 | Scully et al. |
| 3,885,737 A | | 5/1975 | Watkins |
| 3,923,458 A | * | 12/1975 | Moran ............ 422/306 |
| 4,228,124 A | | 10/1980 | Kashihara et al. |
| 5,402,517 A | | 3/1995 | Gillett et al. |
| 5,647,052 A | | 7/1997 | Patel et al. |
| 6,031,967 A | | 2/2000 | Flashinski et al. |
| 6,154,607 A | * | 11/2000 | Flashinski et al. ...... 392/390 |

(Continued)

FOREIGN PATENT DOCUMENTS

WO  WO/03/028775 A1  4/2003

OTHER PUBLICATIONS

International Search Report and Written Opinion for PCT/US/2007/009547 dated Oct. 1, 2007.

*Primary Examiner*—Jill Warden
*Assistant Examiner*—Monzer R Chorbaji (57) ABSTRACT

Disclosed are devices for dispensing air treatment chemicals, and refill units for use therewith. Some of these devices have a well facing the heater and a transparent wall to view the use up of the air treatment chemical. Other of these devices have a refill with wells positioned in opposing directions.

13 Claims, 6 Drawing Sheets

U.S. PATENT DOCUMENTS

| | | |
|---|---|---|
| 6,381,408 B1 | 4/2002 | Jaworski et al. |
| 6,551,560 B1 * | 4/2003 | Flashinski et al. ........... 422/125 |
| 6,581,915 B2 | 6/2003 | Bartsch et al. |
| 6,773,679 B2 * | 8/2004 | Jaworski et al. ............. 422/123 |
| 6,790,670 B2 * | 9/2004 | Munagavalasa et al. ..... 436/164 |
| 6,834,847 B2 | 12/2004 | Bartsch et al. |
| 8,863,957 | 3/2005 | Wycach |
| 2005/0199742 A1 | 9/2005 | Maat |
| 2006/0002102 A1 | 1/2006 | Leonard |

* cited by examiner

AIR TREATMENT DEVICE WITH RESERVOIR REFILL

CROSS-REFERENCE TO RELATED APPLICATIONS

Not applicable

STATEMENT REGARDING FEDERALLY SPONSORED RESEARCH/DEVELOPMENT

Not applicable.

BACKGROUND OF THE INVENTION

The present invention relates to devices that dispense a volatile air treatment chemical by heating a chemical housed in a reservoir. It also relates to improved refills for use with such devices.

The prior art is replete with attempts to efficiently dispense air treatment chemicals such as insect control agents (insecticides, insect repellents, insect growth regulators, attractants, synergists, etc.), fragrances and deodorizers. See e.g. U.S. Pat. No. 6,551,560. The disclosure of this patent, and of all other patents referred to herein, are incorporated by reference as if fully set forth herein.

Conventional devices typically dispense a volatile air treatment chemical by heating a substrate on one side, thereby causing dispensing in an opposed direction. The heating source is typically an electrical heater.

A variety of air treating functions can be achieved with such devices. For example, a volatile insecticide can be dispensed in this way and then used to inhibit mosquito biting in a confined bedroom. Alternatively, a deodorizing or other odor control material can be dispensed to overcome malodors, or to simply provide a desired fragrance.

One problem with such devices is that the chemical to be dispensed, typically coated or impregnated on a porous substrate of some kind, usually rests against or near a heater. The heater heats the substrate, causing the volatized air treatment chemical to be driven off in a direction away from (essentially perpendicular to) a heater surface. See e.g. U.S. Pat. No. 4,228,124.

This can create some inefficiencies. For example, the portion of the material adjacent the heater can act as an insulator for the portion of the substrate which is releasing the active chemical, making control of the dispensing more difficult.

Another problem with such devices is that it may be difficult to determine when such a device is used up. Yet another problem relates to a lack of flexibility where multiple chemicals are to be dispensed which are optimally dispensed under different heating conditions.

Thus, there is a need for improved devices which address these problems.

BRIEF SUMMARY OF THE INVENTION

In one aspect the invention provides a refill suitable to actively dispense a volatile air treatment chemical upon being heated. The refill has a housing having a wall, with one face of the wall configured to be suitable to face a heat source (e.g. an electrical heater), and a second face of the wall (on an opposite side of the wall from the first face), wherein the wall defines a well.

Volatile air treatment chemical is disposed in the well in a manner suitable to volatize out of the well towards the heat source upon being heated by the heat source. The amount of volatile air treatment chemical in the well can be readily viewed through the second face of the wall. Hence, the surface from which the volatile is dispensed is directly heated. Also, a consumer can view how much air treatment chemical is left notwithstanding this construction.

In preferred forms there is a permeable (e.g. semi-permeable) cover over the well for controlling of the rate of dispensing of the volatile air treatment chemical prior to heating. Also, instead of placing the chemical directly in the well, one can place it in a cartridge, with the cartridge inserted in the well. Alternatively, the volatile air treatment chemical may be in solid form, retained within the well by interaction with the sides of the well, by a screen or other cover, or any other conventional way to retain a solid within a cavity.

In another preferred form the refill is capable of dispensing at least two different volatile chemicals. This can be achieved in one way by having the chemicals separately stored (e.g. in separate portions of the same well).

The volatile air treatment chemical may be a liquid or gel material. Also, it can contain a chemical causing a color change upon heating.

In another aspect the invention provides a refill suitable to actively dispense a volatile air treatment chemical upon being heated. The refill has a housing having a wall with one face of the wall configured to be suitable to face a heat source. There is also a well formed along that face. A volatile air treatment chemical is disposed in the well in a manner suitable to volatize out of the well towards the heat source upon being heated by the heat source.

The housing also has a second well configured to face away from the heat source when the first well faces the heat source. A volatile chemical is disposed in the second well in a manner suitable to volatize out of the second well when the refill is positioned adjacent the heat source. Thus, the refill is capable of dispensing an air treatment chemical towards the heat source while simultaneously dispensing a different volatile chemical away from the heat source.

In especially preferred forms of this embodiment the volatile chemical in the second well provides an indication of the extent of use of the refill. This can be because its dispensing rate is coordinated with that of the air treatment chemical and the mere volume left is the indication. Alternatively, it may be because the second chemical has a particular coloration that changes the color in the well as the dispensing takes place.

Alternatively the second well could also contain an air treatment chemical (e.g. a fragrance when the first well has an insecticide), a chemical that facilitates use of the first chemical (e.g. a synergist when the first well has an insecticide), or a material that can be usefully co-dispensed with a material in the first well but that must be kept separate from the first-well material prior to actual dispensing in order to avoid premature chemical or other interaction. Alternatively, first and second well materials may be selected to be simultaneously dispensed but for differing functionalities. An example of the latter would be the simultaneous dispensing of different insecticides, with a first being targeted at one insect and a second targeted at a second insect. For example, one might dispense transfluthrin to control flies and metofluthrin for superior mosquito control.

Any of these chemicals may be positioned in cartridge units, rather than just in wells directly. In any event, either the well or the cartridge can preferably be covered by a permeable (e.g. semi-permeable) membrane which controls volatization rates. These embodiments have an advantage that volatilization can carefully be controlled for two different chemicals.

In still another aspect the invention provides a refill suitable to actively dispense a volatile air treatment chemical upon being heated. The refill has a housing having a wall with a first well facing in one direction, and a second well facing in an opposite direction. There is also a volatile air treatment chemical positioned in at least one of the wells in a manner suitable to volatize out of the well upon being heated by the heat source.

In yet another form the invention provides an air treatment chemical dispensing device. It has a housing, a heater positioned in the housing capable of radiating heat upon being connected to an electrical source, and a refill of any of the above kinds positioned adjacent to the heater. The device is preferably designed to dispense a volatile air treatment chemical selected from the group consisting of insect control agents, fragrances and deodorizers.

It should be appreciated that the refills and devices of the present invention are inexpensive to produce, use heat extremely efficiently, and are capable of providing use-up cue information and/or multiple air treatments simultaneously. A use-up cue is any means for delivering a sensory cue that signals that the refill is exhausted or is nearing exhaustion and should be replaced. The inexpensive cost of such devices is particularly important in developing countries as cost of refills can be a significant barrier to the use of such devices.

The foregoing and other advantages of the present invention will be apparent from the following description. In the description that follows reference is made to the accompanying drawings which form a part thereof, and in which there is shown by way of illustration, and not limitation, expected preferred embodiments of the invention. Such embodiments do not necessarily represent the full scope of the invention, and reference should therefore be made to the claims herein for interpreting the scope of the invention.

DETAILED DESCRIPTION OF THE PREFERRED EMBODIMENTS

Figures 1, 2:
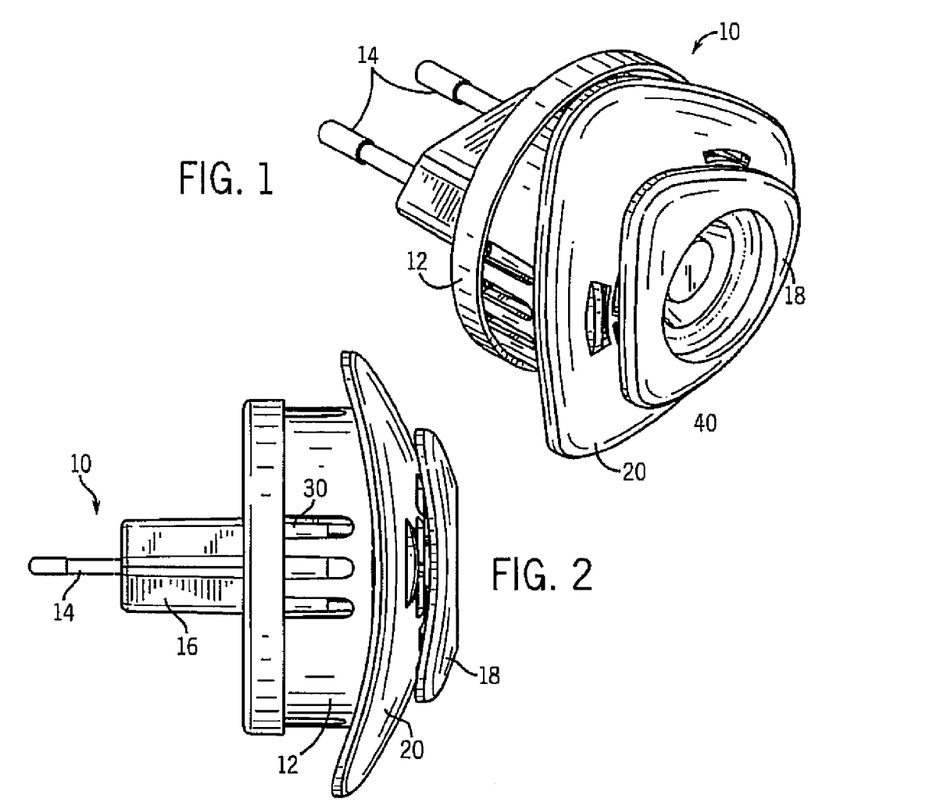
FIG. 1 is a frontal perspective view of an air treatment device of the present invention, with refill attached.
FIG. 2 is a side view thereof.

Referring first to FIG. 1, an air treatment device 10 is shown having a housing 12 with electrical prongs 14 at a rear end 16 and a removable refill 18 attached at an opposing forward end 20. The device 10 is most preferably plugged into an electric socket on a vertical wall. Hence, the directional terms in this patent are used with that type of installation in mind. However, appropriate electric sockets on horizontal or other surfaces may also be used to provide power. Thus, the terms such as "front", "rear", "upper", "lower", and "side" should be interpreted in an analogous manner when the devices are used for that type of installation.

The prongs 14 shown in the figures are merely for purposes of example. Cylindrical prongs of this type are suitable for linking to electric power in some countries. However, in other countries blade prongs, or mixtures of blades, cylinders and other shaped prong elements will be used to supply the linkage to the available power (as is well recognized in the art).

Figure 3:
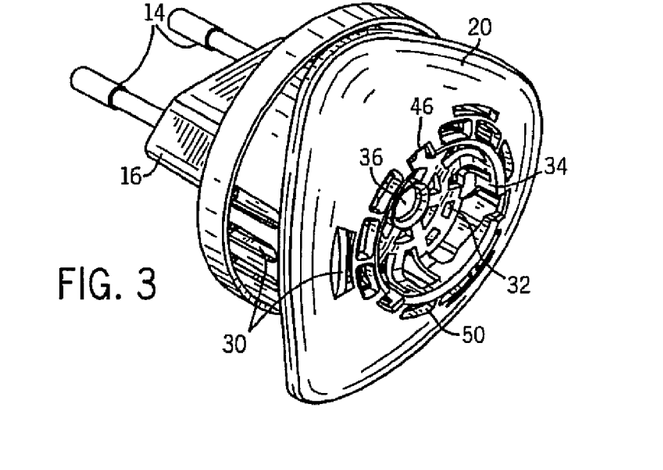
FIG. 3 is a view similar to FIG. 1, but with the refill removed.
Figure 4:
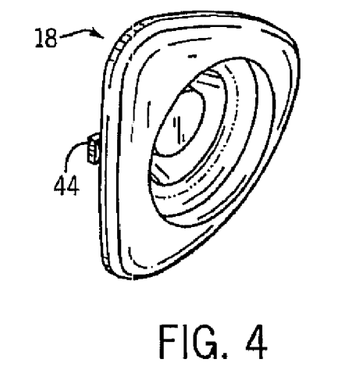
FIG. 4 is a perspective view of the refill alone.
Figure 5:
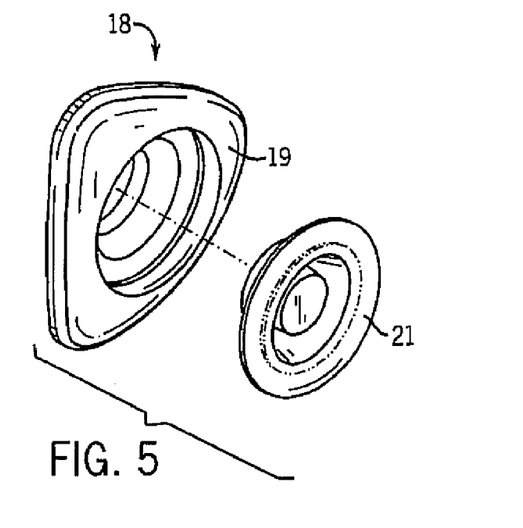
FIG. 5 is an exploded view of the refill.
Figure 6:
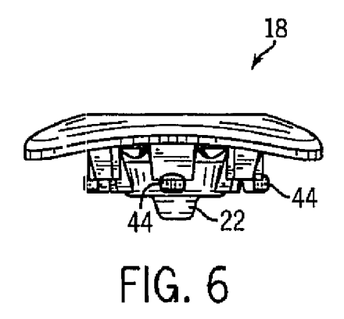
FIG. 6 is a side view of the refill.
Figure 7:
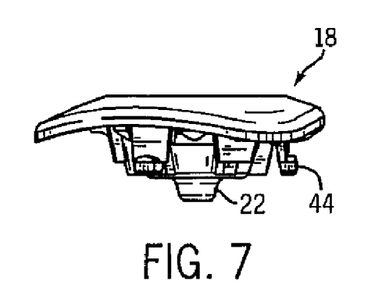
FIG. 7 is another side view of the refill.
Figure 8:
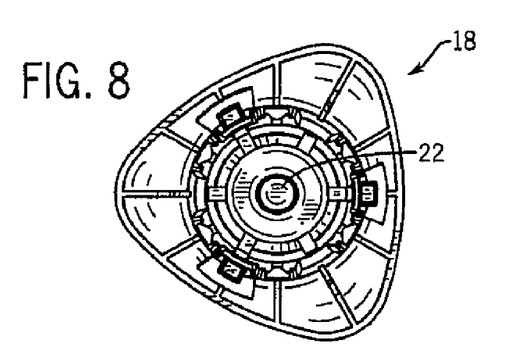
FIG. 8 is a rear view of the refill.

As is evident from FIGS. 2 and 3, the housing 12 preferably has a series of elongated vents 30 on the upper and lower sides of the housing 12. The vents 30 allow in air from the environment and permit it to pass along with the air treatment chemical dispensed from the device 10 through the vents 30 on the upward side of the housing 12. A first well 24 of the refill 18 is preferably positioned closely adjacent the heater 40.

The housing 12 of the overall device 10 preferably has heater 40 positioned proximal to a rearward end of the refill 18. The heater 40 is activated by inserting the electrical prongs 14 into an outlet (not shown).

Figure 9:
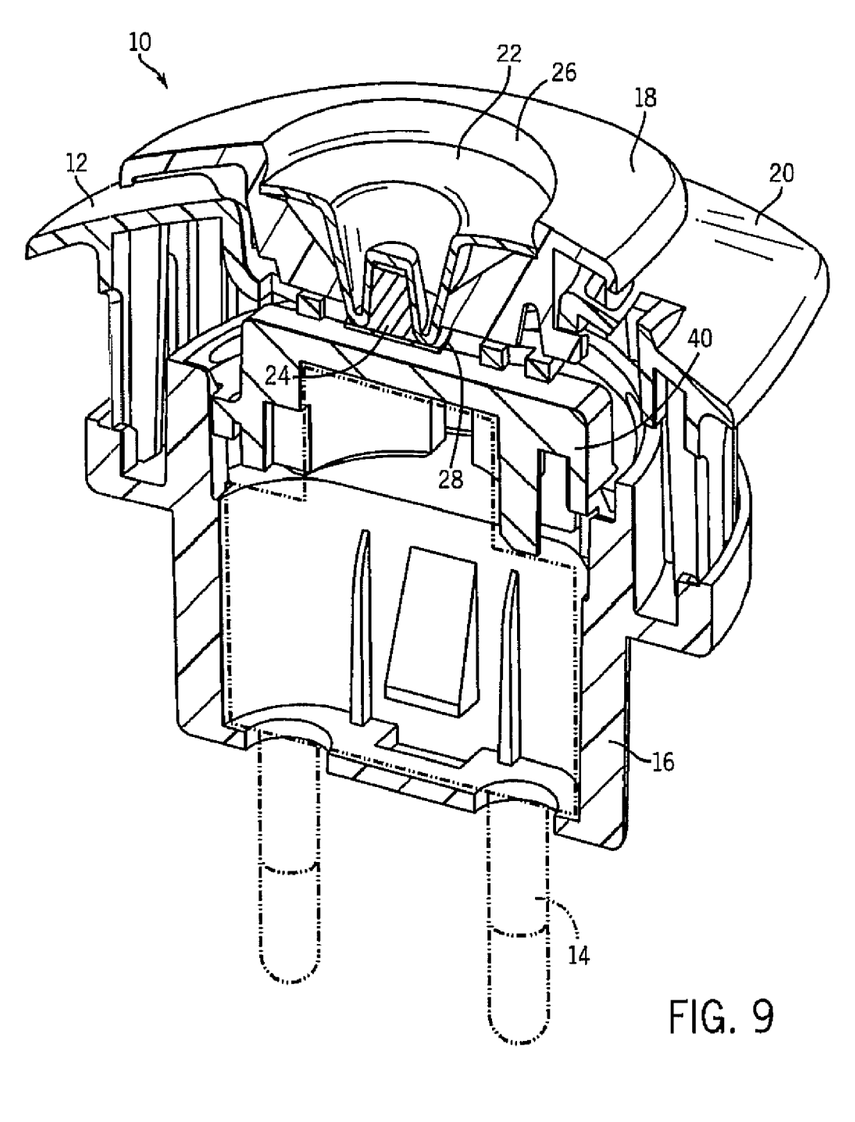
FIG. 9 is a sectional view of the FIG. 1 device.

Heat from the heater 40 contacts the refill 18 either directly (see FIG. 9), or by close convection. However, heat from the heater 40 may also be permitted to pass against other surfaces of the refill 18 through a series of openings 32 and 36 (see FIG. 3).

The refill 18 is designed to be removable from the device 10 so that it can be removed and replaced once used up. It is inserted into the device 10 via connecting legs 44. The legs 44 preferably snap or otherwise position into corresponding grooves 46 in the forward end 20 of the housing.

As will be evident from reviewing FIGS. 4-8, the refill 18 can comprise at least one substantially transparent wall 22. The wall has an inwardly directed tapering cup-shaped well 24 and an outwardly directed, tapering, cup-shaped well 26.

The well 24 preferably contains at least one air treatment chemical 42. The air treatment chemical can be dissolved in a liquid or gel. In a further version a volatile dye can be dissolved with the air treatment chemical and liquid or gel. The air treatment chemical can be secured within the well 24 via a semi-permeable membrane such as 28 in FIG. 10. Prior to use that membrane can further be covered by a peel-off lid (not shown).

Figure 10:
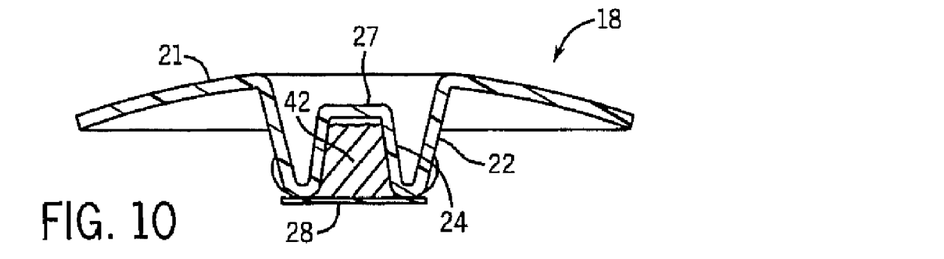
FIG. 10 is an enlarged sectional view of a version of the refill element 21.

The membrane 28 in FIG. 10 is positionable adjacent the heater 40. Hence, when the refill is heated it disperses chemical rearwardly towards the heater 40. This allows a more uniform heating at the time of dispensing, and thus more efficient dispensing. Nevertheless, a consumer can see through the face 27 opposite the heater in order to see how much of the chemical has been used up.

Figure 15:
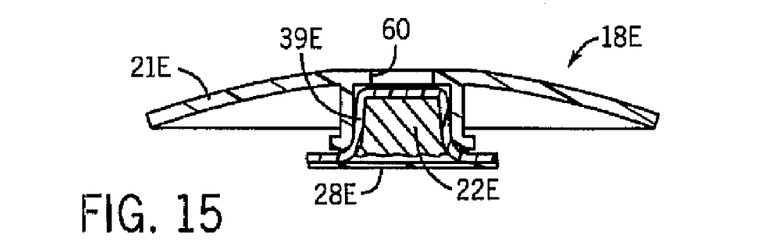
FIG. 15 is a view similar to FIG. 10, but of a sixth embodiment.

As shown in FIG. 15, instead of placing the chemical 42 directly into a well, it can be placed into a cartridge 39E. That cartridge can be wedged into the well 24 by frictional engagement. The wall 21E can in turn be wedged into the holder 19 by a similar frictional engagement. However, other means of securing these parts together are also possible.

The wall 21 can have many forms, as exemplified in FIGS. 10-20. Note that in these figures in each case parts of a similar nature are identified by the same number, but with a different following letter.

In the FIG. 10 embodiment the refill 18 is of a form in which the volatile chemical 42 is directly in the well 24, where dispensing takes place through semi-permeable membrane 28 towards a heater 40.

Figure 11:
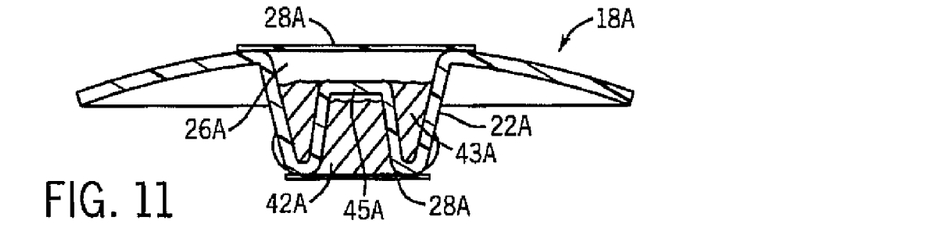
FIG. 11 is a view similar to FIG. 10, but of a second embodiment.

In the FIG. 11 embodiment the device is similar except that outer well 26A is now filled with a second volatile chemical 43A with the chemical filled up to level 45A. The chemical 42A might for example be an insecticide, with the chemical 43A being a volatizable use-up cue.

Figure 12:
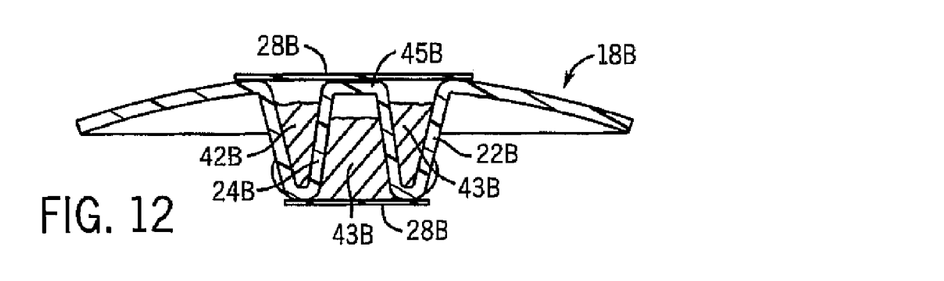
FIG. 12 is a view similar to FIG. 10, but of a third embodiment.

FIG. 12 shows a device similar to FIG. 11, but where the extent 45B of the well 24B is now such as to support the semi-permeable membrane 28B.

Figure 13:
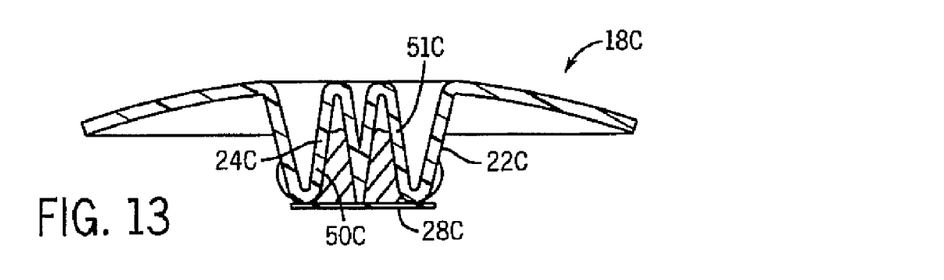
FIG. 13 is a view similar to FIG. 10, but of a fourth embodiment.

In the FIG. 13 embodiment the structure is similar to the FIG. 10 embodiment except that the well 24C is now split into two wells 50 and 51C, where each well contains a different volatile.

Figure 14:
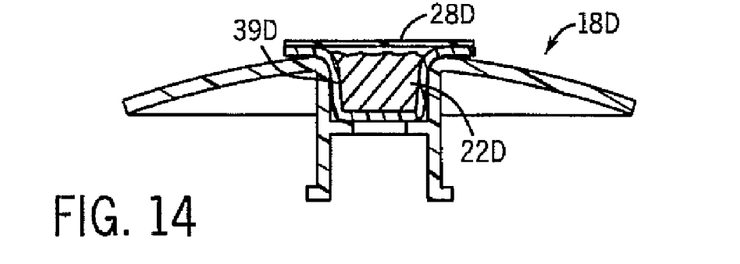
FIG. 14 is a view similar to FIG. 10, but of a fifth embodiment.

In the FIG. 14 embodiment the refill 18D permits alternative mounting of a refill cartridge in either an outward or inward direction.

In the FIG. 15 embodiment the cartridge is mounted inward, and there is a peep hole 60 to facilitate viewing the remaining amount of air treatment chemical in the device.

Figure 16:
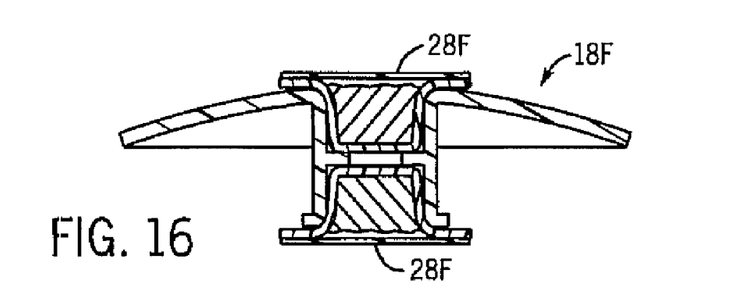
FIG. 16 is a view similar to FIG. 10, but of a seventh embodiment.

The FIG. 16 embodiment is similar to the FIG. 14 embodiment, except that two cartridges are mounted, one inward and one outward, preferably with different chemicals volatizable from each.

Figure 17:
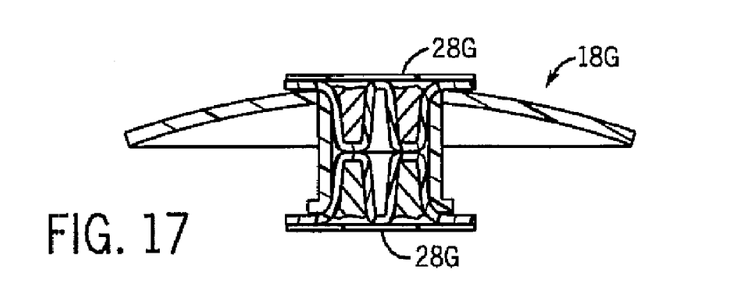
FIG. 17 is a view similar to FIG. 10, but of an eighth embodiment.

The FIG. 17 embodiment is similar to the FIG. 16 embodiment, except that the wells of both cartridges are split so as to provide four different volatizable chemicals. For example, one well can dispense an insecticide, another a synergist, another a fragrance, and the last a use-up cue.

Figure 18:
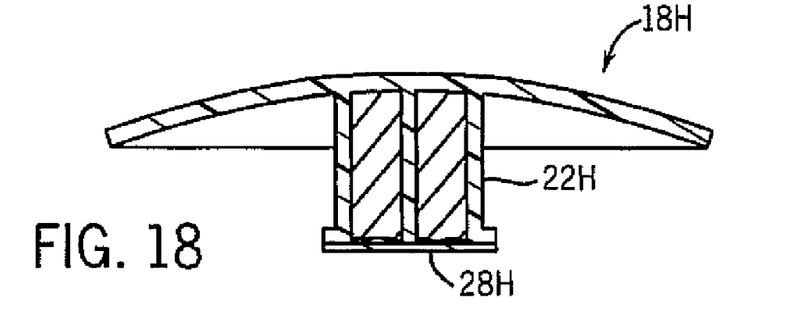
FIG. 18 is a view similar to FIG. 10, but of a ninth embodiment.

The FIG. 18 embodiment is similar to the FIG. 13 embodiment, except that the wall structure is slightly different.

Figure 19:
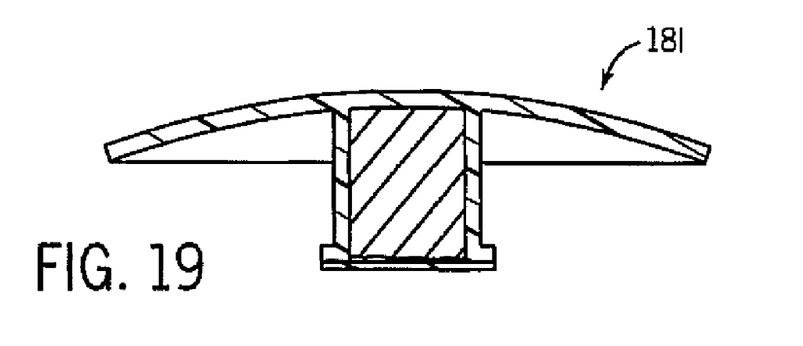
FIG. 19 is a view similar to FIG. 10, but of a tenth embodiment.
Figure 20:
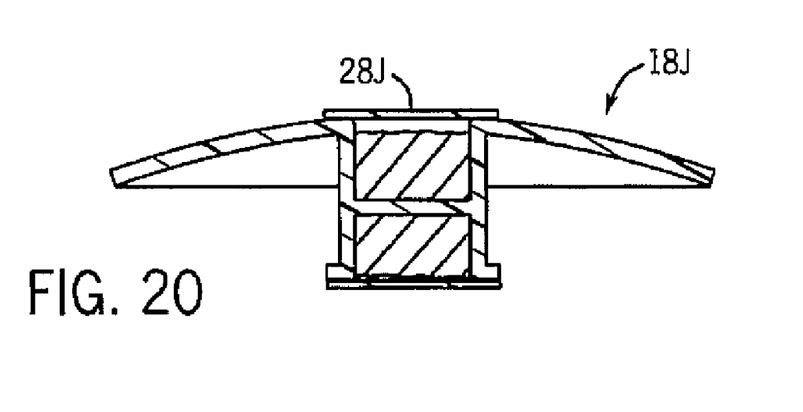
FIG. 20 is a view similar to FIG. 10, but of an eleventh embodiment.

The FIG. 19 structure is similar to the FIG. 10 structure except that there is no permeable membrane due to the use of a more rigid volatizable material, The FIG. 20 structure is analogous to the FIG. 16 structure except that it uses a membrane covering a well at one end and no membrane at the other.

It should be appreciated that the wall component of the refills can be formed as a one-piece injection molded or thermoformed structure. Preferably, heat resistant plastics are used for this purpose.

The wells are preferably cup-shaped, but may have other configurations (e.g. tapered cups, rectangular wells, irregular shapes). A particularly preferred transparent material for the refill is recycled polythethylene terephthalate.

Suitable semi-permeable materials well known to the art, such as low density polyethylenes, may be used for the semi-permeable membranes of the invention. Such membranes, along with a removable sealing layer, are available from Pechiney Plastic Packaging, Inc., of Chicago, Ill.

When the air treatment chemical is an insecticide and/or insect repellent, organic phosphorus insecticides, lipidamide insecticides, natural repellents as citronella oil, natural pyrethrins and pyrethrum extract, and synthetic pyrethroids are preferred. Suitable synthetic pyrethroids are acrinathrin, allethrin as D-allethrin, Pynamin™, benfluthrin, bifenthrin, bioallethrin as Pynamin Forte™, S-bioallethrin, esbiotrin, esbiol, bisoresmethrin, cycloprothrin, cyfluthrin, beta-cyfluthrin, cyhalothrin, lambda-cyhalothrin, cypermethrin, alpha-cypermethrin, beta-cypermethrin, cyphenothrin, deltamethrin, empenthrin, esfenvalerate, fenpropathrin, fenvalerate, flucythrinate, taufluvalinate, kadetrin, permethrin, phenothrin, prallethrin as Etoc™, resmethrin, tefluthrin, tetramethrin, tralomethrin, metofluthrin, or transfluthrin. Other volatile insecticides, such as those described in U.S. Pat. No. 4,439,415, can also be employed.

In particularly preferred versions the volatile insecticide is selected from the group consisting of transfluthrin, metofluthrin, vapothrin, permethrin, prallethrin, tefluthrin and esbiothrin. Transfluthrin is presently the most preferred insecticide. Metofluthrin is also an especially advantageous insecticide.

Possible solvents for carrying these air treatment chemicals include, but are not limited to, ISOPAR™C, ISOPAR™E, ISOPAR™L, heptane, methanol, acetone, ethanol, isopropyl alcohol, dodecene and tetraydrofuran. ISOPAR™C, ISOPAR™E and ISOPAR™L are hydrocarbon solvents of varying chain length and are available from Exxon Chemical Company.

One particularly desirable air treatment chemical for mosquito control is 50 weight percent transfluthrin dissolved in ISOPAR™C hydrocarbon.

A wide variety of volatile fragrances may be used which may optionally also have insect control attributes. Alternatively, some fragrances may be selected that provide a deodorizing function (e.g. certain terpenes). For example, various natural and artificial perfumes may be used. Non-limiting examples of these perfumes include animal-based and plant-based natural perfumes, and artificial perfumes such as alcohols, phenols, aldehydes, ketones, terpenes, and esters.

When an volatile air treatment chemical is a disinfectant, preferred disinfectants include, but are not limited to, glycols, trimethylene and dipropylene. Organic acids may also be used.

While the preferred embodiments of the present invention have been described above, it should be appreciated that the invention could be used in a variety of other embodiments. For example, instead of dissolving the air treatment chemical in a liquid or gel, the active chemical may be used alone.

Thus, the principles of the present invention can be applied in a wide variety of other ways apart from those specifically noted herein. Still other modifications may be made without departing from the spirit and scope of the invention. Thus, the claims (rather than just the preferred embodiments) should be reviewed in order to understand the ill scope of the invention.

INDUSTRIAL APPLICABILITY

The present invention provides devices for dispensing air treatment chemicals, and refills for use therewith.

We claim:

1. A refill suitable to actively dispense a volatile air treatment chemical upon being heated, the refill comprising:
a housing having an essentially transparent wall with one rear face of the wall configured to be suitable to face a heat source, and a front face of the wall on an essentially opposite side of the wall from the rear face, wherein the wall defines a reservoir well configured to be suitable to open rearwardly toward the heat source;
volatile air treatment chemical being disposed in the well in a manner suitable to volatize rearwardly out of the well towards the heat source as it passes out from the refill upon being heated by the heat source;

the housing also having a second well configured to be suitable to face frontally away from the heat source when the reservoir well faces the heat source, such that the reservoir well will be positioned between the heat source and the second well when the second well is positioned adjacent the heat source;

wherein the amount of volatile air treatment chemical in the reservoir well can be viewed from a frontal side of the wall through the front face of the wall.

2. The refill claim 1, further comprising a permeable cover over the reservoir well for controlling of the rate of dispensing of the volatile air treatment chemical prior to heating.

3. The refill of claim 1, wherein a cartridge is inserted in the reservoir well, with the volatile air treatment chemical being positioned in the cartridge.

4. The refill of claim 1, wherein the refill is capable of dispensing at least two different volatile chemicals from the reservoir well, with the chemicals being separately stored in separate portions of the reservoir well.

5. The refill of claim 1, wherein the volatile air treatment chemical is a liquid or gel material.

6. The refill of claim 1, wherein the volatile air treatment chemical undergoes a color change upon heating.

7. A refill suitable to actively dispense a volatile air treatment chemical upon being heated, the refill comprising:

a housing having a wall with one rear face of the wall configured to be suitable to face a heat source;

a first well formed along said face, the first well being configured to be suitable to open toward the heat source;

volatile air treatment chemical being disposed in the first well in a manner suitable to volatize out of the first well rearwardly towards the heat source as it passes out from the refill upon being heated by the heat source;

the housing also having a second well configured to be suitable to face frontally away from the heat source when the first well faces the heat source, such that the first well will be positioned between the heat source and the second well when the second well is positioned adjacent the heat source;

a volatile chemical being disposed in the second well in a manner suitable to volatize frontally out of the second well when the refill is positioned adjacent the heat source;

wherein the refill is capable of dispensing an air treatment chemical towards the heat source while simultaneously dispensing a different volatile chemical away from the heat source.

8. The refill of claim 7, wherein the volatile chemical in the second well is an indicator of the extent of use of the refill.

9. The refill of claim 7, wherein the volatile chemical in the second well is also an air treatment chemical.

10. The refill of claim 7, wherein both the volatile air treatment chemical and the volatile chemical in the second well are each positioned in cartridge units.

11. The refill of claim 7, wherein both the volatile air treatment chemical and the volatile chemical in the second well are each covered by a permeable membrane which controls volatization rates.

12. An air treatment chemical dispensing device comprising:

a housing;

a heater positioned in the housing, wherein the heater is capable of radiating heat upon being connected to an electrical source; and a refill positioned adjacent to the heater, the refill comprising:

a carrier having a wall with a first well facing in one direction and opening towards the heater and a second well facing in an opposite direction; and a volatile air treatment chemical being positioned in at least one of the wells in a manner suitable to volatize out of the well towards the heater as it passes out from the refill upon being heated by the heater;

wherein at least one of the wells is positioned between the other of the wells and the heater.

13. The device of claim 12, wherein the device dispenses a volatile air treatment chemical selected from the group consisting of insect control agents, fragrances and deodorizers.

\* \* \* \* \*

UNITED STATES PATENT AND TRADEMARK OFFICE
CERTIFICATE OF CORRECTION

PATENT NO. : 7,651,666 B2  Page 1 of 1
APPLICATION NO. : 11/379495
DATED : January 26, 2010
INVENTOR(S) : Adair et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 561 days.

Signed and Sealed this

Twenty-third Day of November, 2010

David J. Kappos
*Director of the United States Patent and Trademark Office*